US011793966B2

(12) United States Patent
Falk

(10) Patent No.: US 11,793,966 B2
(45) Date of Patent: Oct. 24, 2023

(54) VENTILATION SYSTEM AND METHOD

(71) Applicant: GE Precision Healthcare LLC, Wauwatosa, WI (US)

(72) Inventor: Steven M. Falk, Baltimore, MD (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 322 days.

(21) Appl. No.: 17/196,624

(22) Filed: Mar. 9, 2021

(65) Prior Publication Data

US 2021/0299389 A1 Sep. 30, 2021

Related U.S. Application Data

(60) Provisional application No. 63/000,955, filed on Mar. 27, 2020.

(51) Int. Cl.
| | |
|---|---|
| *A61M 16/08* | (2006.01) |
| *A61M 16/06* | (2006.01) |
| *A61M 16/00* | (2006.01) |

(52) U.S. Cl.
CPC .... *A61M 16/0833* (2014.02); *A61M 16/0666* (2013.01); *A61M 2016/0027* (2013.01); *A61M 2205/3334* (2013.01); *A61M 2205/587* (2013.01)

(58) Field of Classification Search
CPC .......... A61M 16/0833; A61M 16/0666; A61M 2016/0027; A61M 2205/3334; A61M 2205/587; A61M 39/10; A61M 16/20; A61M 16/201; A61M 16/205; A61M 16/202
See application file for complete search history.

(56) References Cited

U.S. PATENT DOCUMENTS

| | | | | |
|---|---|---|---|---|
| 3,564,273 A | * | 2/1971 | Cockrell | F01D 17/24 290/40 R |
| 4,667,658 A | * | 5/1987 | Guibert | A23L 3/365 601/16 |
| 5,057,817 A | * | 10/1991 | Berube | G08B 29/16 340/517 |
| 2018/0272101 A1 | * | 9/2018 | Arnott | A61M 16/202 |

FOREIGN PATENT DOCUMENTS

| WO | WO-2012030232 A1 | * | 3/2012 | ........... A61B 5/0836 |
|---|---|---|---|---|
| WO | WO-2013154439 A1 | * | 10/2013 | ........... A61B 5/0836 |

* cited by examiner

*Primary Examiner* — Kendra D Carter
*Assistant Examiner* — Maap Ahmed Ellabib
(74) *Attorney, Agent, or Firm* — ANDRUS INTELLECTUAL PROPERTY LAW, LLP

(57) ABSTRACT

A T-piece for controlling ventilation support to a patient includes a t-shaped body having a gas source connection port, an interface connection port, and a positive end-expiratory pressure (PEEP) control port. A PEEP adjuster cap is connected to the PEEP control port and has a bypass hole to allow gas to exit the T-piece and configured such that when the bypass hole is closed substantially all gas received at the gas source connection port is directed to the patient and when the bypass hole is open at least a portion of the gas received at the gas source connection port exits through the bypass hole to maintain PEEP to the patient. A bypass cover is automatically operated by an actuator circuit to close the bypass hole to enable delivery PIP to the patient and to open the bypass hole to effectuate PEEP delivery to the patient.

20 Claims, 2 Drawing Sheets

VENTILATION SYSTEM AND METHOD

CROSS REFERENCE TO RELATED APPLICATION

The present application claims priority to U.S. Provisional Application Ser. No. 63/000,955, filed Mar. 27, 2020, the disclosure of which is incorporated herein by reference.

BACKGROUND

The present disclosure is related to the field of patient respiratory support, and more particularly to ventilation systems and methods for providing constant positive end-expiratory pressure (PEEP), Hi-flow PEEP, and positive-pressure ventilation (PPV).

Over the course of a medical treatment, a patient may require some form of respiratory support provided by a ventilator or may require multiple different types of respiratory support which is generally provided by different types of ventilation devices in different settings. Respiratory support may include assisted breathing, where supplemental pressure and gas flow are provided to the patient to complete an effective respiratory cycle—e.g., constant positive end-expiratory pressure (PEEP), Hi-flow PEEP, and positive-pressure ventilation (PPV). Other forms of respiratory support include mechanical ventilation, whereby the ventilator also initiates the respiratory phase of each respiratory cycle, such as delivered to the patient via an endotracheal tube.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a T-piece for controlling ventilation support to a patient includes a t-shaped body having a gas source connection port configured to receive a gas flow from a gas source, an interface connection port configured to connect to a patient interface device, and a positive end-expiratory pressure (PEEP) control port. A PEEP adjuster cap is connected to the PEEP control port, the PEEP adjuster cap having a bypass hole to allow gas to exit the T-piece and configured such that when the bypass hole is closed substantially all gas received at the gas source connection port is directed to the patient, and when the bypass hole is open, at least a portion of the gas received at the gas source connection port exits through the bypass hole to maintain PEEP to the patient. The T-piece is configured such that the bypass hole can be closed to deliver peak inspiratory pressure (PIP). A bypass cover is closeable to close the bypass hole to enable delivery PIP to the patient and openable to open the bypass hole to effectuate PEEP delivery to the patient. An actuator circuit is configured to automatically open and close the bypass cover.

A system for providing ventilation assistance to a patient includes a gas source, a patient interface device, and a T-piece comprising a t-shaped body including a gas source connection port configured to receive gas from a gas source hose, an interface connection port configured to connect to a patient interface device, and a PEEP control port. A PEEP adjuster cap is connected to the PEEP control port, the PEEP adjuster cap having a bypass hole to allow gas to exit the T-piece and configured such that when the bypass hole is closed substantially all gas received at the gas source connection port is directed to the patient, and when the bypass hole is open at least a portion of the gas received at the gas source connection port exits through the bypass hole to maintain PEEP to the patient. A bypass cover is closeable to close the bypass hole so as to deliver PIP to the patient and openable to open the bypass hole so as to deliver PEEP to the patient. An actuator circuit is configured to automatically open and close the bypass cover.

Various other features, objects, and advantages of the invention will be made apparent from the following description taken together with the drawings.

DETAILED DESCRIPTION

Figure 1:
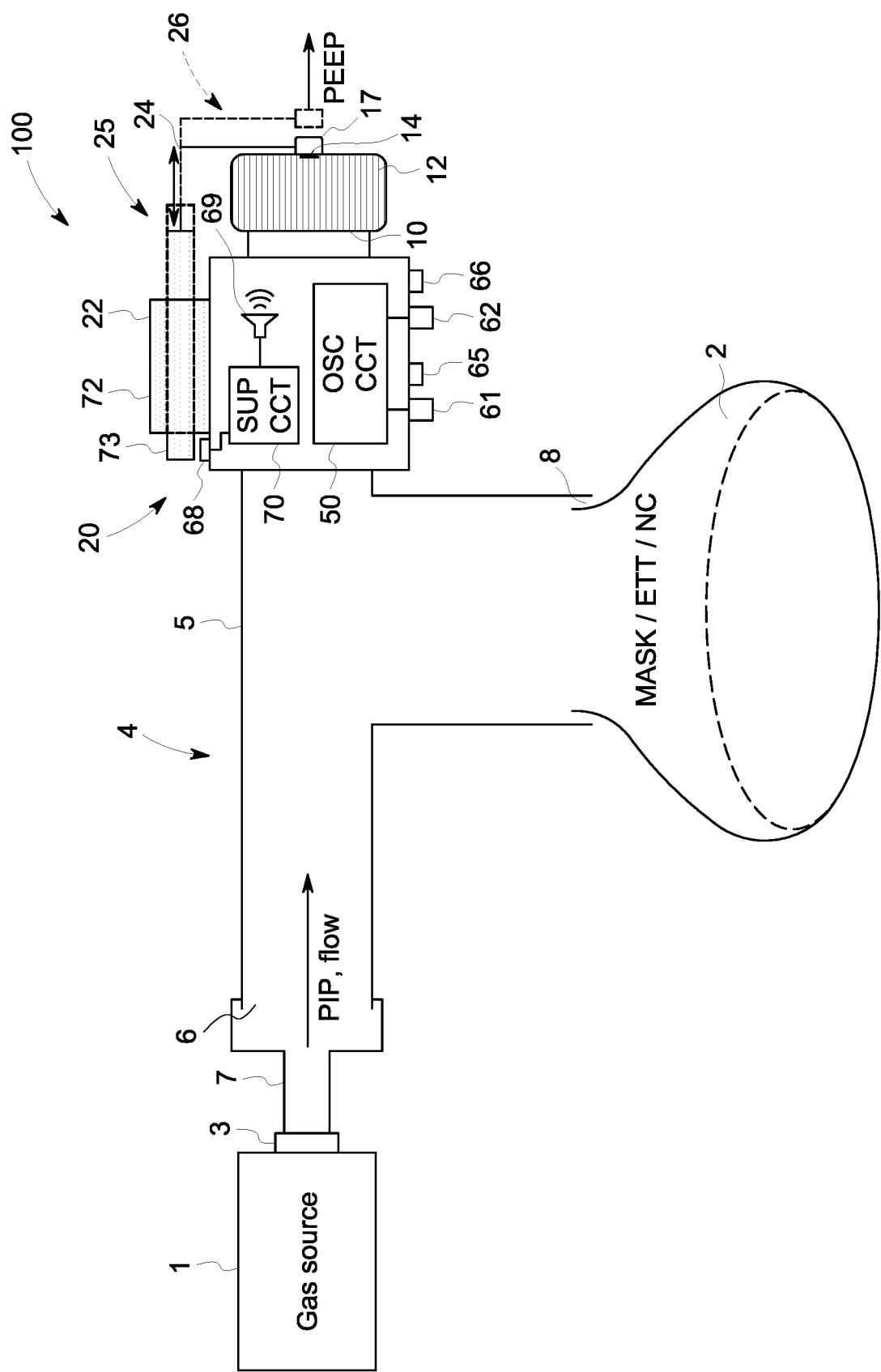
FIG. 1 depicts an exemplary embodiment of a T-piece for controlling ventilation support in accordance with the present disclosure.

The inventor has recognized that systems and methods need to be developed to provide non-invasive ventilation (NIV) as an early intervention for patients who need respiratory care. NIV includes oxygen delivery, constant positive end-expiratory pressure (PEEP), Hi-flow PEEP, and noninvasive positive-pressure ventilation (NIPPV). NIPPV is delivery of positive-pressure ventilation without the need for an endotracheal tube. In place of the tube may be a tight-fitting nasal or facial mask. However, in certain embodiments the disclosed system may also be used to provide positive pressure ventilation with an endotracheal tube.

Furthermore, the inventor has recognized a need for an NIV system and solution that does not require use of a ventilator system capable of providing full mechanical ventilation support to an intubated patient. When ventilators are in short supply, such as due to an influx of patients in need of respiratory care, NIV systems can supplement and reduce the demand for ventilators by providing respiratory support for less critical patients. Furthermore, the inventor has recognized a need for an NIV system that can provide respiratory support to less critical patients as an earlier intervention that may support and preserve the patients' lung function and delay or prevent the need for intubation and use of a ventilator system for such patients. Furthermore, the inventor has recognized that NIV and the disclosed device and system can also be used for weaning a patient off of full ventilation support and can provide an intermediate step that may allow earlier termination of ventilation and may free up ventilators for cleaning and use with subsequent patients.

The disclosed system and method for providing NIV, which can also be used with an endotracheal tube to ventilate a patient, provide peak inspiratory pressure (PIP) during the inspiratory phase of the patient's respiration and PEEP during the expiratory phase of the patient's respiration. The disclosed system is operable with any gas source with variable flow regulation and a flow meter. For example, a resuscitation unit or any gas source (tank, wall source, etc.) with a variable flow meter and a regulator may be utilized. The gas source may provide $O_2$, air, or a mixture.

The disclosed system and method for providing ventilation includes a T-piece connectable between a gas supply and a patient interface device, such as a facial mask, nasal cannula, or an endotracheal tube. The T-piece includes a t-shaped body having three ports, including a gas source connection port configured to connect to the gas source hose to receive gas therefrom, a interface connection port configured to connect to the mask or other patient interface, and a positive end-expiratory pressure (PEEP) control port. A PEEP adjustor cap is connected to the PEEP control port, the PEEP adjustor cap having a bypass hole, or opening, to allow gas to exit the T-piece and configured such that when the bypass hole is closed substantially all gas received at the gas source connection port is directed to the patient, and when the bypass hole is open at least a portion of the gas received at the gas source connection port exits through the bypass hole to maintain PEEP to the patient. The T-piece is configured such that the bypass hole can be closed to deliver peak inspiratory pressure (PIP) and then opened to deliver PEEP. In order to open and close the bypass hole, a bypass cover closable to close the bypass hole so as to deliver PIP to the patient and openable to open the bypass hole so as to deliver PEEP to the patient. An actuator circuit is configured to automatically open and close the bypass cover.

In certain embodiments, the actuator circuit includes a linear actuator. The linear actuator may be connected to the bypass cover by a rigid connector. For instance, the linear actuator may include a return spring solenoid having an activated position that closes the bypass cover over the bypass hole and a deactivated position that opens the bypass cover over the bypass hole. The actuator circuit may include a pulse width modulation (PWM) circuit configured to control an open-close duty cycle of the bypass cover and one or more control inputs configured to enable a clinician to set and/or adjust the open-close duty cycle. For example, the control input may be a knob or a rotatable element controllable to adjust a potentiometer within the actuator circuit. For example, a first knob may be provided that is controllable to adjust the open portion of the duty cycle, the inspiratory time, and a second knob controllable to adjust a closed portion of the duty cycle, the exhalation time.

The system may also include a supervisory circuit configured to monitor each of an open duration, or inspiratory time, and a close duration, or exhalation time, of the open-close duty cycle and determine whether the open duration or the close duration exceeds a predetermined maximum duration. The supervisory circuit is configured such that if the predetermined maximum duration is exceeded, then the actuator circuit defaults to holding the bypass cover in the open position. For example, where the actuator circuit is a return spring solenoid, it may default to the deactivated position where the bypass hole is uncovered. The supervisory circuit may further include an alert device configured to generate an auditory alert and/or a visual alert, such as a buzzer and/or a light emitting diode (LED). If either the open duration or the close duration exceeds the predetermined maximum duration, then an alert may be generated to draw attention to the malfunction. Alternatively or additionally, one or more LEDs may be associated with the actuator circuit and/or the supervisory circuit that are configured to illuminate to indicate whether the bypass cover is open or closed.

FIG. 1 illustrates one embodiment of a system 100 for providing positive pressure ventilation to a patient. The gas supply hose 7 providing gas from a gas source is connected to the mask 2 via a T-piece 4. The mask 2 is placed over the patient's nose and mouth, as is customary. Alternatively, the patient interface device may be something other than a mask, such as a nasal cannula or even an endotracheal tube.

The T-piece 4 connects between the mask 2 and the gas supply hose 7. The gas supply hose 7 connects to a gas supply 1, such as an air supply, controllable as described above. The T-piece 4 has a t-shaped body 5 forming three ports, including a gas supply connection port 6 that connects to the air supply hose 7, an interface connection port 8 that connects to the mask 2 or other patient interface device, and a positive end-expiratory pressure (PEEP) control port 10. As is standard, a PEEP adjustor cap 12 is provided at the PEEP control port 10. The PEEP adjustor cap 12 has a bypass hole 14, or opening, for expiration of breath. The PEEP adjustor cap 12 is used to adjust the minimum pressure (the PEEP pressure) to prevent the lungs from collapsing. Specifically, the PEEP adjustor cap 12 is adjustable to control an outflow pressure to control PEEP. When bypass hole 14 is covered, all air is directed from the gas supply 1 to the patient. When the bypass hole 14 is uncovered, much of the supplied gas bypasses the mask 2 and exits through the hole 14. Thus, when the bypass hole 14 is covered, PIP is provided for the duration that the hole is covered or closed—i.e., an inspiratory period. When the bypass hole 14 is uncovered or open, then PEEP is provided for an expiratory period.

The disclosed system includes a bypass cover 17 and actuator circuit 20 that automatically cover and uncover the bypass hole 14 periodically so as to provide alternating PIP and PEEP at a rate corresponding with an appropriate respiration rate for the patient. For example, the bypass cover may be a small rubber or plastic disk or flap that is moved onto and off of the bypass hole 14 in the cap 12. In certain examples, the bypass cover 17 and actuator circuit 20 are contained in a disposable module attachable to the t-shaped body 5 and/or to the PEEP adjustor cap 12. For example, the disposable module may be clipped or strapped to the t-shaped body 5 of the T-piece 4.

In certain embodiments, the actuator circuit 20 includes a linear actuator 22, such as a spring-loaded solenoid. The linear actuator 22 may be connected to the bypass cover 17 by a rigid connector 24 such that linear movement by the actuator 22 moves the bypass cover 17 from a closed position 25 where PIP is provided to an open position 26 where PEEP is provided. In one embodiment, the linear actuator 22 is a return spring solenoid having an activated position that is the closed position 25 that closes the bypass cover 17 over the bypass hole 14 and a deactivated position that opens the bypass cover 17 to uncover the bypass hole 14. The return spring solenoid linear actuator 22 has a solenoid 72 that, when activated, moves the ferromagnetic cylinder 73, or bar, to a position of minimal reluctance, which in the depicted arrangement is the closed position 25. When the solenoid 72 is not activated, i.e., no current is passing, then the bar 73 is pushed back to the deactivated position, which in this example is the open position 26, by a spring. One benefit of the depicted embodiment is that, if the solenoid 72 fails or some other element of the actuator circuit 20 fails, the bypass cover will revert to the open position 26 such that PEEP (rather than PIP) is maintained.

The actuator circuit 20 includes a clock or oscillator mechanism to control the open-close duty cycle of the bypass cover 17. In one embodiment, the oscillator mechanism is configured such that the duty cycle is adjustable to enable the clinician can adjust tidal volume and respiration rate delivered to the patient. In one embodiment, both the inspiration time that the bypass cover 17 is held in the closed position 25 and the exhalation time that the bypass cover 17 is held in the closed position are adjustable. The ratio of the inhalation time to the exhalation time yields the open-close duty cycle. The flow rate is controllable via the flow controller 3 providing a variable flow meter and a flow regulator to enable flow rate control by the clinician, which are well known. The flow rate is set at the flow controller 3 and the inhalation time and exhalation time, and thus the open-close duty cycle, are set by the clinician on first and second control inputs 61 and 62 provided on the module. Thus, by setting flow rate and inspiratory time, the clinician can control tidal volume delivered to the patient.

Figure 2:
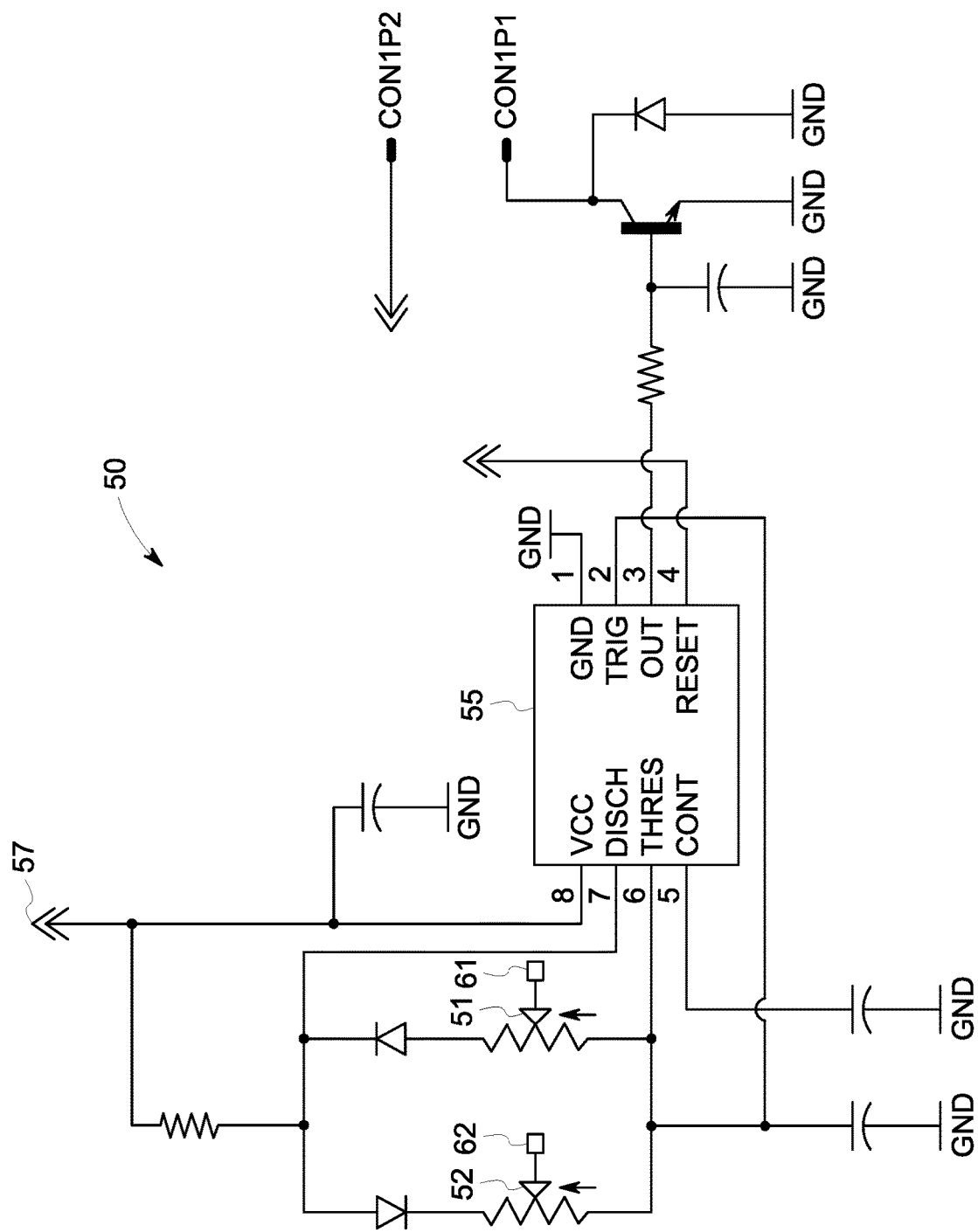
FIG. 2 depicts an exemplary oscillation circuit for inclusion in a T-piece in accordance with the present disclosure.

In one embodiment, the actuator circuit 20 includes a pulse width modulation (PWM) circuit that controls the open-close duty cycle of the bypass cover 17. FIG. 2 is a circuit diagram representing an exemplary oscillator circuit 50 being a PWM circuit that powers the solenoid 72 of the linear actuator 22 and thus controls the open-close duty cycle. The oscillator circuit 50, such as a PWM circuit, includes an oscillator or timer 55, such as a 555 timer chip, configured to modulate its output duty cycle in response to one or more potentiometers. In the depicted example, the oscillator control chip 55 has the following pins: ground (GND), trigger (TRIG), output (OUT), reset (RESET), control (CONT), threshold (THRES), discharge (DISCH), and power input (VCC). The control inputs 61 and 62, such as knobs, connect to variable resistor potentiometers 51 and 52, which adjust the open portion of the duty cycle and the closed portion of the duty cycle, respectively. The oscillator circuit 50 provides output connections CON1P1 and CON1P2.

The oscillator circuit 50 receives input power from power source 57, which in various embodiments may be via a lightening connector, a USBC connector, or other connector protocol providing a 5V or other voltage level. Alternatively, the power connection may provide a 12 V connection to power the oscillator circuit 50 and other elements connected to the actuator circuit 20. In one embodiment, one or more LEDs 65, 66 may be connected to the actuator circuit, such as powered by the oscillator circuit 50. The one or more LEDs 65, 66 may be configured to indicate whether the bypass cover is opened or closed. For example, one of the LEDs 65, 66 may be simultaneously powered with the solenoid and thus illumination of that LED 65, 66 may provide an easy visual indicator to a clinician (from a distance) that the bypass cover 17 is closed and PIP is being provided.

Alternatively or additionally, one or more of the LEDs 65, 66 may be controlled by a supervisory circuit 70 configured to monitor the bypass cover 17 position to make sure that it is operating properly. One important function of the supervisory circuit 70 is to make sure that PIP is not being delivered for too long, which can over expand the patient's lungs and cause adverse health effects for the patient. The supervisory circuit 70 is configured to monitor at least the close duration that the bypass cover 17 is in the closed position 25, and in some embodiments is configured to monitor each of the open duration and the close duration of the open-close duty cycle to detect whether either or the combination exceeds a predetermined maximum duration. To provide just one example, the maximum duration may be 3 seconds or 4 seconds; however, the supervisory circuit 70 may be configured to permit longer or shorter predetermined maximum durations of PIP or PEEP. If the supervisory circuit 70 may be configured such that if it detects that one of the open or close durations reaches the predetermined maximum duration, an alert is generated and/or power to the solenoid 72 is cut such that the bypass cover 17 is maintained in the open position. It will be understood by an ordinary skilled person in view of this disclosure that the supervisory circuit 70 and the oscillation circuit 50 may be integrated into one control circuit or one control device, or may be separate elements that may or may not be communicatively connected.

A sensor 68 is configured to sense the position of the actuator 22 or the bypass cover 17 so as to determine whether the cover is in the open position 26 or closed position 25. In the depicted example, the sensor 68 is configured to sense an actuator position, and specifically a position of the cylinder 73. For example, the sensor may be an optical sensor configured to optically detect the cylinder 73 position, such as an optical bubble sensor. One exemplary such optical bubble sensor is the BE-A301 optical bubble sensor by Panasonic, which may be positioned to receive and optically sense the cylinder 73 only when the linear actuator 22 is in the closed position. In such an embodiment, when the linear actuator 22 is in the open position 26 then the cylinder 73 would on be in the optical path of the sensor 68 and the open position 26 is determined accordingly. In another exemplary embodiment, the sensor 68 may be a magnetic sensor that magnetically detects the position of the cylinder 73. In still other embodiments, the sensor 68 may detect a position of the cover 17. For example, the sensor 68 may be a contact sensor located on the cap 12 adjacent to an outer rim of the bypass hole 14. To provide just one example, the sensor 68 may comprise two electrical contacts on either side of the bypass hole 14 and the bypass cover 17 may include a conductive trace or be comprised of a conductive material that provides electrical connection between the two traces when the bypass cover 17 is in the closed position 25.

One or more alert devices may be included and controllable by the supervisory circuit if one of the close duration or the open duration exceeds the predetermined maximum. The alert device may include, for example, a buzzer 69 that generates an auditory alert and/or an LED 65, 66 that is illuminated to provide a visual alert when the malfunction is detected.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A T-piece for controlling ventilation support to a patient, the T-piece comprising:
a t-shaped body including a gas source connection port configured to receive gas from a gas source, an interface connection port configured to connect to a patient interface device, and a positive end-expiratory pressure (PEEP) control port;
a PEEP adjustor cap connected to the PEEP control port, the PEEP adjustor cap having a bypass hole to allow gas to exit the T-piece and configured such that when the bypass hole is closed substantially all gas received at the gas source connection port is directed to the patient, and when the bypass hole is open at least a portion of the gas received at the gas source connection port exits through the bypass hole to maintain PEEP to the patient;

a bypass cover closable to close the bypass hole so as to deliver peak inspiratory pressure (PIP) to the patient and openable to open the bypass hole so as to deliver PEEP to the patient; and an actuator circuit configured to automatically open and close the bypass cover.

2. The T-piece of claim 1, wherein the actuator circuit includes a linear actuator configured to move the bypass cover relative to the bypass hole.

3. The T-piece of claim 2, further comprising a rigid connector connecting the linear actuator to the bypass cover to translate the movement of the linear actuator thereto.

4. The T-piece of claim 2, wherein the linear actuator includes a return spring solenoid having an activated position that closes the bypass cover over the bypass hole and a deactivated position that opens the bypass cover over the bypass hole.

5. The T-piece of claim 1, wherein the actuator circuit includes a pulse width modulation (PWM) circuit configured to control an open-close duty cycle of the bypass cover.

6. The T-piece of claim 5, further comprising at least one control input movable by a clinician to adjust the open-close duty cycle.

7. The T-piece of claim 6, wherein the at least one control input is a knob controllable to adjust a potentiometer within the actuator circuit.

8. The T-piece of claim 7, further comprising a first knob controllable to adjust the open portion of the duty cycle and a second knob controllable to adjust a closed portion of the duty cycle.

9. The T-piece of claim 1, further comprising a supervisory circuit configured to monitor each of an open duration and a close duration of an open-close duty cycle and detect if the open duration or the close duration exceeds a predetermined maximum duration.

10. The T-piece of claim 9, further comprising a sensor configured to sense whether the actuator circuit and/or the bypass cover are in an open position or a closed position.

11. The T-piece of claim 9, further comprising an alert device configured to generate an auditory alert and/or a visual alert if either the open duration or the close duration exceeds the predetermined maximum duration.

12. The T-piece of claim 9, further comprising at least one light emitting diode (LED), wherein the supervisory circuit is configured to illuminate the at least one LED to indicate whether the bypass cover is open or closed.

13. The T-piece of claim 1, wherein the bypass cover and actuator circuit are contained in a disposable module attachable to the t-shaped body and/or to the PEEP adjustor cap.

14. The T-piece of claim 1, wherein the patient interface device is one of a facial mask, nasal cannula, or endotracheal tube.

15. A system for providing ventilation assistance to a patient, the system comprising:

a gas source;

a patient interface device;

a T-piece comprising a t-shaped body including a gas source connection port configured to receive gas from a gas source, an interface connection port configured to connect to the patient interface device, and a positive end-expiratory pressure (PEEP) control port;

a PEEP adjustor cap connected to the PEEP control port, the PEEP adjustor cap having a bypass hole to allow gas to exit the T-piece and configured such that when the bypass hole is closed substantially all gas received at the gas source connection port is directed to the patient, and when the bypass hole is open at least a portion of the gas received at the gas source connection port exits through the bypass hole to maintain PEEP to the patient;

a bypass cover closable to close the bypass hole so as to deliver peak inspiratory pressure (PIP) to the patient and openable to open the bypass hole so as to deliver PEEP to the patient; and an actuator circuit configured to automatically open and close the bypass cover.

16. The system of claim 15, wherein the actuator circuit includes a linear actuator configured to move the bypass cover relative to the bypass hole.

17. The system of claim 16, further comprising a rigid connector connecting the linear actuator to the bypass cover to translate the movement of the linear actuator thereto.

18. The system of claim 17, wherein the linear actuator includes a return spring solenoid having an activated position that closes the bypass cover over the bypass hole and a deactivated position that opens the bypass cover over the bypass hole.

19. The system of claim 16, wherein the actuator circuit includes a pulse width modulation (PWM) circuit configured to control the linear actuator to effectuate an open-close duty cycle of the bypass cover, wherein the open-close duty cycle is adjustable by a clinician.

20. The system of claim 19, further comprising a supervisory circuit configured to monitor each of an open duration and a close duration of an open-close duty cycle and detect if the open duration or the close duration exceeds a predetermined maximum duration.

* * * * *